US009293060B2

(12) United States Patent
Hanina et al.

(10) Patent No.: US 9,293,060 B2
(45) Date of Patent: Mar. 22, 2016

(54) APPARATUS AND METHOD FOR RECOGNITION OF PATIENT ACTIVITIES WHEN OBTAINING PROTOCOL ADHERENCE DATA

(75) Inventors: Adam Hanina, New York, NY (US); Gordon Kessler, Mt. Kisco, NY (US)

(73) Assignee: Ai Cure Technologies LLC, Mt. Kisco, NY (US)

( * ) Notice: Subject to any disclaimer, the term of this patent is extended or adjusted under 35 U.S.C. 154(b) by 103 days.

(21) Appl. No.: 12/815,037

(22) Filed: Jun. 14, 2010

(65) Prior Publication Data
US 2011/0275051 A1     Nov. 10, 2011

Related U.S. Application Data

(60) Provisional application No. 61/331,872, filed on May 6, 2010.

(51) Int. Cl.
    *G09B 25/00*     (2006.01)
    *G09B 19/00*     (2006.01)
    *G06F 19/00*     (2011.01)

(52) U.S. Cl.
    CPC ............ *G09B 19/00* (2013.01); *G06F 19/3418* (2013.01); *G06F 19/3456* (2013.01)

(58) Field of Classification Search
    CPC . G09B 19/00; G09B 19/3418; G09B 19/3456
    USPC ........................................................ 434/365
    See application file for complete search history.

(56) References Cited

U.S. PATENT DOCUMENTS

| 3,814,845 | A | | 6/1974 | Hurlbrink et al. | |
|---|---|---|---|---|---|
| 5,065,447 | A | | 11/1991 | Barnsley et al. | |
| 5,441,047 | A | * | 8/1995 | David et al. | 600/483 |
| 5,486,001 | A | * | 1/1996 | Baker | 473/266 |
| 5,544,649 | A | * | 8/1996 | David et al. | 600/301 |
| 5,619,991 | A | * | 4/1997 | Sloane | 600/300 |
| 5,646,912 | A | | 7/1997 | Cousin | |
| 5,752,621 | A | | 5/1998 | Passamante | |
| 5,764,296 | A | | 6/1998 | Shin | |
| 5,810,747 | A | * | 9/1998 | Brudny et al. | 600/595 |
| 5,911,132 | A | * | 6/1999 | Sloane | 705/3 |
| 5,961,446 | A | | 10/1999 | Beller et al. | |
| 6,126,449 | A | | 10/2000 | Burns | |
| 6,151,521 | A | | 11/2000 | Guo et al. | |
| 6,233,428 | B1 | | 5/2001 | Fryer | |
| 6,283,761 | B1 | * | 9/2001 | Joao | 434/236 |
| 6,380,858 | B1 | | 4/2002 | Yarin et al. | |
| 6,409,661 | B1 | | 6/2002 | Murphy | |
| 6,421,650 | B1 | * | 7/2002 | Goetz et al. | 705/3 |

(Continued)

OTHER PUBLICATIONS

"Super-Resolution", *Wikipedia*, (Oct. 5, 2010).

(Continued)

*Primary Examiner* — Timothy Musselman
*Assistant Examiner* — Alvin Carlos
(74) *Attorney, Agent, or Firm* — Fish & Richardson P.C.

(57) ABSTRACT

A medication confirmation method and apparatus. The method of an embodiment of the invention includes the steps of capturing one or more video sequences of a user administering medication, storing the captured one or more video sequences, and comparing at least one of the stored video sequences with a corresponding one or more prerecorded video sequences to confirm that the user has properly administered the medication.

20 Claims, 7 Drawing Sheets

(56) References Cited

U.S. PATENT DOCUMENTS

| | | | |
|---|---|---|---|
| 6,461,162 B1* | 10/2002 | Reitman et al. | 434/247 |
| 6,483,993 B1 | 11/2002 | Misumi et al. | |
| 6,484,144 B2 | 11/2002 | Martin et al. | |
| 6,535,637 B1 | 3/2003 | Wootton et al. | |
| 6,611,206 B2* | 8/2003 | Eshelman et al. | 340/573.1 |
| 6,705,991 B2* | 3/2004 | Bardy | 600/300 |
| 6,879,970 B2 | 4/2005 | Shiffman et al. | |
| 6,988,075 B1 | 1/2006 | Hacker | |
| 7,184,047 B1 | 2/2007 | Crampton | |
| 7,184,075 B2 | 2/2007 | Reiffel | |
| 7,256,708 B2* | 8/2007 | Rosenfeld et al. | 340/870.01 |
| 7,277,752 B2 | 10/2007 | Matos | |
| 7,304,228 B2 | 12/2007 | Bryden et al. | |
| 7,307,543 B2* | 12/2007 | Rosenfeld et al. | 340/870.01 |
| 7,317,967 B2* | 1/2008 | DiGianfilippo et al. | 700/265 |
| 7,340,077 B2 | 3/2008 | Gokturk | |
| 7,369,919 B2 | 5/2008 | Vonk et al. | |
| 7,395,214 B2 | 7/2008 | Shillingburg | |
| 7,415,447 B2 | 8/2008 | Shiffman et al. | |
| 7,448,544 B1 | 11/2008 | Louie et al. | |
| 7,562,121 B2* | 7/2009 | Berisford et al. | 709/206 |
| 7,627,142 B2 | 12/2009 | Kurzweil et al. | |
| 7,657,443 B2 | 2/2010 | Crass et al. | |
| 7,692,625 B2 | 4/2010 | Morrison et al. | |
| 7,740,013 B2 | 6/2010 | Ishizaki et al. | |
| 7,747,454 B2 | 6/2010 | Bartfield et al. | |
| 7,761,311 B2 | 7/2010 | Clements et al. | |
| 7,769,465 B2 | 8/2010 | Matos | |
| 7,774,075 B2 | 8/2010 | Lin et al. | |
| 7,874,984 B2 | 1/2011 | Elsayed et al. | |
| 7,881,537 B2 | 2/2011 | Ma et al. | |
| 7,908,155 B2 | 3/2011 | Fuerst et al. | |
| 7,912,733 B2* | 3/2011 | Clements et al. | 705/2 |
| 7,956,727 B2 | 6/2011 | Loncar | |
| 7,983,933 B2 | 7/2011 | Karkanias et al. | |
| 8,321,284 B2* | 11/2012 | Clements et al. | 705/20 |
| 2001/0049673 A1* | 12/2001 | Dulong et al. | 707/1 |
| 2001/0056358 A1 | 12/2001 | Dulong et al. | |
| 2002/0026330 A1 | 2/2002 | Klein | |
| 2002/0093429 A1 | 7/2002 | Matsushita et al. | |
| 2002/0143563 A1 | 10/2002 | Hufford et al. | |
| 2003/0164172 A1 | 9/2003 | Chumas et al. | |
| 2003/0190076 A1 | 10/2003 | Delean | |
| 2003/0225325 A1 | 12/2003 | Kagermeier et al. | |
| 2004/0100572 A1 | 5/2004 | Kim | |
| 2004/0107116 A1* | 6/2004 | Brown | 705/2 |
| 2004/0155780 A1 | 8/2004 | Rapchak | |
| 2005/0144150 A1 | 6/2005 | Ramamurthy et al. | |
| 2005/0149361 A1* | 7/2005 | Saus et al. | 705/3 |
| 2005/0180610 A1 | 8/2005 | Kato et al. | |
| 2005/0182664 A1 | 8/2005 | Abraham-Fuchs et al. | |
| 2005/0234381 A1* | 10/2005 | Niemetz et al. | 604/4.01 |
| 2005/0267356 A1* | 12/2005 | Ramasubramanian et al. | 600/411 |
| 2006/0066584 A1 | 3/2006 | Barkan | |
| 2006/0218011 A1 | 9/2006 | Walker et al. | |
| 2006/0238549 A1 | 10/2006 | Marks | |
| 2007/0008112 A1 | 1/2007 | Covannon et al. | |
| 2007/0008113 A1 | 1/2007 | Spoonhower et al. | |
| 2007/0016443 A1 | 1/2007 | Wachman et al. | |
| 2007/0030363 A1 | 2/2007 | Cheatle et al. | |
| 2007/0118054 A1 | 5/2007 | Pinhas et al. | |
| 2007/0118389 A1* | 5/2007 | Shipon | 705/1 |
| 2007/0194034 A1 | 8/2007 | Vasiadis | |
| 2007/0233035 A1 | 10/2007 | Wehba et al. | |
| 2007/0233049 A1 | 10/2007 | Wehba et al. | |
| 2007/0233050 A1 | 10/2007 | Wehba et al. | |
| 2007/0233281 A1 | 10/2007 | Wehba et al. | |
| 2007/0233520 A1 | 10/2007 | Wehba et al. | |
| 2007/0233521 A1 | 10/2007 | Wehba et al. | |
| 2007/0273504 A1 | 11/2007 | Tran | |
| 2007/0276270 A1 | 11/2007 | Tran | |
| 2008/0000979 A1 | 1/2008 | Poisner | |
| 2008/0086533 A1 | 4/2008 | Neuhauser et al. | |
| 2008/0093447 A1 | 4/2008 | Johnson et al. | |
| 2008/0114226 A1* | 5/2008 | Music et al. | 600/323 |
| 2008/0114490 A1 | 5/2008 | Jean-Pierre | |
| 2008/0138604 A1 | 6/2008 | Kenney et al. | |
| 2008/0140444 A1 | 6/2008 | Karkanias et al. | |
| 2008/0162192 A1 | 7/2008 | Vonk et al. | |
| 2008/0178126 A1 | 7/2008 | Beeck et al. | |
| 2008/0201174 A1 | 8/2008 | Ramasubramanian et al. | |
| 2008/0219493 A1 | 9/2008 | Tadmor | |
| 2008/0275738 A1* | 11/2008 | Shillingburg | 705/3 |
| 2008/0281630 A1 | 11/2008 | Sekura | |
| 2008/0290168 A1 | 11/2008 | Sullivan et al. | |
| 2008/0297589 A1 | 12/2008 | Kurtz et al. | |
| 2008/0303638 A1 | 12/2008 | Nguyen et al. | |
| 2009/0012818 A1 | 1/2009 | Rodgers | |
| 2009/0018867 A1 | 1/2009 | Reiner | |
| 2009/0024112 A1* | 1/2009 | Edwards et al. | 604/890.1 |
| 2009/0043610 A1 | 2/2009 | Nadas et al. | |
| 2009/0048871 A1 | 2/2009 | Skomra | |
| 2009/0095837 A1 | 4/2009 | Lindgren | |
| 2009/0128330 A1 | 5/2009 | Monroe | |
| 2009/0159714 A1 | 6/2009 | Coyne, III et al. | |
| 2009/0217194 A1 | 8/2009 | Martin et al. | |
| 2009/0245655 A1 | 10/2009 | Matsuzaka | |
| 2010/0042430 A1 | 2/2010 | Bartfeld | |
| 2010/0050134 A1 | 2/2010 | Clarkson | |
| 2010/0057646 A1 | 3/2010 | Martin et al. | |
| 2010/0092093 A1 | 4/2010 | Akatsuka et al. | |
| 2010/0136509 A1 | 6/2010 | Mejer et al. | |
| 2010/0138154 A1 | 6/2010 | Kon | |
| 2010/0255598 A1 | 10/2010 | Melker | |
| 2010/0262436 A1 | 10/2010 | Chen et al. | |
| 2010/0316979 A1* | 12/2010 | Von Bismarck | 434/127 |
| 2011/0021952 A1 | 1/2011 | Vallone | |
| 2011/0119073 A1 | 5/2011 | Hanina et al. | |
| 2011/0153360 A1 | 6/2011 | Hanina et al. | |
| 2011/0161109 A1 | 6/2011 | Pinsonneault et al. | |
| 2011/0195520 A1 | 8/2011 | Leider et al. | |
| 2011/0275051 A1 | 11/2011 | Hanina et al. | |
| 2012/0075464 A1 | 3/2012 | Derenne et al. | |

OTHER PUBLICATIONS

"PCT Search report and written opinion", (Jan. 12, 2011),1-9.

"Non-Final Office Action from PTO", (Oct. 13, 2011),1-74.

Danya International, Inc., *Pilot Study Using Cell Phones for Mobile Direct Observation Treatment to Monitor Medication Compliance of TB Patients*, Mar. 20, 2009, www.danya.com/MDOT.asp.

University of Texas, *GuideView*, Mar. 15, 2007, http://www.sahs.uth.tmc.edu/MSriram/GuideView/.

Chen, Pauline W., *Texting as a Health Tool for Teenagers*, The New York Times, Nov. 5, 2009, http://www.nytimes.com/2009/11/05/health/05chen.html?_r=1&emc=.

Whitecup, Morris S., *2008 Patient Adherence Update: New Approaches for Success*, Guideline Trend Report, Oct. 2008.

Osterberg, Lars and Blaschke, Terrence, *Adherence to Medication*, New England Journal of Medicine 2005; 353:487-97, Aug. 4, 2005.

World Health Organization, *Global Tuberculosis Control: A Short Update to the 2009 Report*, 2009.

Non-Final Office Action from PTO, (U.S. Appl. No. 12/898,338), (Jun. 19, 2012), 1-16.

PCT Search report and written opinion, (PCT/US12/41785, (Aug. 17, 2012),1-10.

Non-final Office Action from PTO—(U.S. Appl. No. 12/620,686) (Dec. 21, 2011), 1-78.

Non-final Office Action from PTO—(U.S. Appl. No. 12/646,383) (Dec. 22, 2011), 1-78.

Final Office Action from PTO—(U.S. Appl. No. 12/646,603) (Feb. 1, 2012), 1-17.

Non-final Office Action from PTO—(U.S. Appl. No. 12/728,721) (Jan. 6, 2012), 1-19.

Final Office Action from PTO—(U.S. Appl. No. 12/620,686) (May 8, 2012), 1-23.

Final Office Action from PTO—(U.S. Appl. No. 12/646,383) (May 8, 2012), 1-22.

International Preliminary Report on Patentability, (PCT/US2010/056935) (May 31, 2012), 1-8.

(56) References Cited

OTHER PUBLICATIONS

Final Office Action from PTO—(U.S. Appl. No. 12/728,721) (Apr. 12, 2012), 1-28.
International Search Report, (PCT/US11/35093) (Dec. 9, 2011), 1-8.
Non-Final Office Action from PTO, (U.S. Appl. No. 13/558,377), (Oct. 22, 2012), 1-21.
Non-Final Office Action from PTO, (U.S. Appl. No. 13/558,380), (Oct. 4, 2012), 1-20.
Non-Final Office Action from PTO (U.S. Appl. No. 12/899,510), (Jan. 23, 2013), 1-20.
PCT Search report and written opinion, (PCT/US11/54666), (Feb. 28, 2012), 1-13.
Final Office Action from PTO (U.S. Appl. No. 12/898,338), (Nov. 9, 2012), 1-12.
PCT Search report and written opinion, (PCT/US11/54668), Feb. 28, 2012, 1-12.
Non-Final Office Action from PTO, (U.S. Appl. No. 13/189,518), (Dec. 21, 2012), 1-10.
PCT Search report and written opinion, (PCT/US2012/051554), (Oct. 19, 2012), 1-12.
Huynh et al., Real time detection, tracking and recognition of medication intake. World Academy of Science, Engineering and Technology 60 (2009), 280-287.
PCT Search report and written opinion, (PCT/US12/59139), (Dec. 18, 2012), 1-15.
Final Office Action from PTO, (U.S. Appl. No. 13/558,377), May 7, 2013, 1-29.
Final Office Action from PTO, (U.S. Appl. No. 13/588,380), (Mar. 1, 2013), 1-27.
Non-Final Office Action from PTO, (U.S. Appl. No. 12/646,603), (Jun. 13, 2013), 1-16.
Non-Final Office Action from PTO, (U.S. Appl. No. 12/728,721), (May 9, 2013), 1-25.
Final Office Action from PTO, (U.S. Appl. No. 12/899,510), (Aug. 28, 2013).
Final Office Action from PTO, (U.S. Appl. No. 13/189,518), (Jul. 23, 2013), 1-16.
Non-Final Office Action from PTO, (U.S. Appl. No. 13/235,387), (Sep. 12, 2013), 1-16.
PCT Search report and written opinion, (PCT/US12/42843), (Aug. 31, 2012), 1-8.
PCT Search report and written Opinion, (PCT/US13/20026), (Aug. 5, 2013), 1-14.
Ammouri, S.; Biloduau, G. -A, "Face and Hands Detection and Tracking Applied to the Monitoring of Medication Intake," Computer and Robot Vision, 2008. CRV '08. Canadian Conference on, vol. no., pp. 147, 154, May 28-30, 2008.
Batz, et al. "A computer Vision System for Monitoring Medicaiton Intake," in Proc. IEEE 2nd Canadian Conf. on Computer and Robot Vision, Victoria, BC, Canada, 2005, pp. 362-369.
Valin, et al. "Video Surveillance of Medication intake", Int. Conf. of the IEEE Engineering in Medicine and Biology Society, New York City, USA, Aug. 2006.
Bilodeau et al. Monitoring of Medication Intake Using a Camera System. Journal of Medical Systems 2011. [retrieved on Feb. 18, 2013] Retrieved from ProQuest Technology Collection.
Mintchell, "Exploring the Limits of Machine Vision", Automating World, Oct. 1, 2011.
U.S. Appl. No. 13/235,387, filed Sep. 18, 2011, Hanina et al.
U.S. Appl. No. 13/674,459, filed Nov. 12, 2012, Hanina et al.

\* cited by examiner

FIGURE 7

APPARATUS AND METHOD FOR RECOGNITION OF PATIENT ACTIVITIES WHEN OBTAINING PROTOCOL ADHERENCE DATA

CROSS REFERENCE TO RELATED APPLICATIONS

This application claims the benefit of U.S. Provisional Patent Application Ser. No. 61/331,872 filed May 6, 2010, titled APPARATUS AND METHOD FOR RECOGNITION OF PATIENT ACTIVITIES WHEN OBTAINING PROTOCOL ADHERENCE DATA, the entire contents thereof being incorporated herein by reference.

FIELD OF THE INVENTION

This invention relates generally to patient compliance in medication administration protocol scenarios, and more particularly to an apparatus and method for the collection, analysis and transmission of data related to patient movements related to such medication administration in order to improve adherence with prescribed drug protocols in accordance therewith. The invention further relates to a tracking and guidance training system for individuals taking prescribed medication, and may also provide incentives such as reminding a patient of the benefits of a particular medication, providing the patient monetary points or other remuneration on the screen, and one or more reminders to take an appropriate medication.

BACKGROUND OF THE INVENTION

Dr Lars Osterberg, M. D. and Dr, Terence Blaschke have reported in the New England Journal of Medicine, *Adherence to Medication*, (N Engl J Med 2005; 353:487-97) 2005 an alarming lack of adherence to required medication protocol, further noting that while the average rates of adherence in clinical trials is categorized as "high", this number still comprises only rates of 43 to 78 percent. Most importantly, the authors note "The ability of physicians to recognize nonadherence is poor, and interventions to improve adherence have had mixed results." *Adherence*, p. 487. The authors conclude "Poor adherence to medication regimens is common, contributing to substantial worsening of disease, death and increased healthcare costs." *Adherence*, p. 494. *The Trend Repot Series, 2008 Patient Adherence Update: New Approaches for Success*, October 2008, report similar discouraging statistics. This broad range may possibly contribute to the public confidence in the FDA approval process and the importance of continued surveillance of a drug throughout the process. Furthermore, it may help to explain why, according to the Journal of the American Medical Association (JAMA May 1, 2002), one out of every five new drugs that comes to market in the US is found to have serious or life-threatening adverse effects—unknown or undisclosed at the time of approval. It is against this backdrop of poor adherence, and potential danger to patients, that the present invention operates.

It has been widely recognized that methods and systems for insuring proper medication ingestion or administration by individuals are very important in defending against unnecessary sickness, deaths and other problems. Giving instructions and then letting patients fend for themselves has been shown not to work particularly well. This is because it is not only the improper ingestion of medicines that is the primary cause of medical danger. Rather, an overall lack of sufficient patient guidance is also part of the problem. Further, the inability to confirm a proper prescription regimen being provided to a user in the first place may cause a number of other problems with the use of such medication. As has been shown in regards to various public health medication administration situation, such as administration of tuberculosis medication by the WHO, Directly Observed Treatment (DOT) improves compliance of patients. *Global Tuberculosis Control: A Short Update to the* 2009 *Report*, World Health Organization, 2009. As is shown in this report, funding for implementing DOT programs is high. Thus, the ability to implement such a program with less of a financial burden would be desirable.

Traditionally, participants attend introductions and follow ups for clinical trials in-person. Other patients attempting to adhere to a particular medication protocol similarly are given a prescription and a particular set of instructions from a prescribing medical provider or prescribing doctor, and then compliance is measured at a next visit with that prescribing professional through traditional methods of pill counting, and patient interviews. Thus, data collection is similarly limited to patient visits, rather than on a daily basis. These old methods such as patient questioning and pill counting have been proven to be inadequate measures of adherence and offer no information on dose timing and drug holidays (omission of medication for three or more sequential days).

Compliance technologies can increase the statistical power of clinical trials. Through the use of such technology, clinical events can be precisely linked to medication use history. Captured data can be linked to other sources such as EDC, patient diaries and data collected by the physician. Technologies can create many possibilities for remote visits and data capture. While smart packaging technologies exist such as RFID-enabled computer chip technology, smart blister packs and MEMS caps (microprocessor in a bottle cap), they are: a) invasive and need to be physically attached to the medications; b) are non-conclusive regarding compliance—a patient may activate the technology without ingestion of the medication; c) remain largely unadopted in clinical trials by the pharmaceutical and biotech companies due to their high cost; and d) take a longer time to implement. Further, electronic patient diaries allow for ease of entry of data by a patient. These diaries, however, are still subject to issues related to compliance with medication adherence. Thus, even if a patient is meticulous about entering information into the diary, and thus complying with the requirements for data entry, there is still no guarantee that they are properly taking medication at prescribed times.

Jo Carol et al. stated that "The most reliable method for research purposes, although not practical in a clinical setting, may be a combination approach that includes pill counts, patient self-report, and electronic monitoring." (Carol J. et al, Patterns to Antiretroviral Medication, The Value of Electronic Monitoring, AIDS, 17 (12), pp 1, 763-767, October 2003. To date, technologies alone have only been used to monitor compliance rather than to encourage it. Furthermore, there has been no comprehensive system provided that allows for the management of multiple patients and multiple patient populations. While current technology may allow poor compliers to be recognized, as will be described below, the proposed apparatus and method of the present invention will help to encourage pharmaceutical compliance and tackle some of the problems that are encountered in the clinical trial process in particular, and the medication protocol monitoring problem in general.

A number of systems exist that provide instructions to a user regarding when to take a medication and records when the user indicates that a medication has been taken. U.S. Pat. No. 7,359,214 describes such a system. A device is provided that provides instruction to a patient regarding medications to take. Furthermore, the system may provide a method for determining that the prescription is appropriate given the patient's conditions, and other medications he or she may already be taking. The system may monitor the dispensing of medicine in accordance with a predetermined treatment protocol. While such a system provides many improvements for easing a burden on the patient, this system suffers in many ways and in particular in ways relevant to the administration of clinical trials and other active patient monitoring of medication adherence.

Most importantly, this system provides no mechanism for actually confirming that a patient is in fact ingesting or otherwise properly administering required medication as required in a clinical drug trial, as prescribed by a prescribing physician in the case where adherence to a particular regimen may prove to be critical to efficacy of the prescription regimen, in various public health scenarios, in situations where failure to keep up a prescription regimen can potentially harm a population as a whole, such as the generation of antibiotic-resistant bacteria strains, in various disease management scenarios, or in home care situations where maintaining proper control of administering healthcare professionals is critical. Further, while the system may be sufficient for one who is in full possession of their mental faculties, any individual who may have difficulty following directions, or one who is actively avoiding medication may still not be taking required medication after it is dispensed. Thus, participants may be forgetful, visually impaired, or otherwise do not believe in the benefit of taking such medication, and may thus not properly log medication administration. Furthermore, the system requires preloading of various medications into a dispenser, and thus likely requires regular visits by an administering manager to be sure appropriate medications are in fact properly loaded therein. It is surely possible that an inexperienced user may place incorrect medications into the device, or may somehow provide incorrect dosages into the device. Additionally, for potentially more complex regimens, there is no method provided for insuring that a user is able to follow such a protocol, and to thereafter confirm that the user has in fact taken all required medications in accordance with any provided instructions or the like, or has taken the medications according to one or more specifications or followed suggested procedures. Finally, this system is expensive and requires constant maintenance to confirm that the various mechanical parts are in working order.

U.S. patent application Ser. No. 11/839,723, filed Aug. 16, 2007, titled Mobile Wireless Medication Management System provides a medication management system employing mobile devices and an imaging technology so that a user is able to show a pill to be taken to the system, and the system can then identify the medication. Patient histories are available to an administrator, including various vital signs as measured by the system. Images may also be taken of the patient, provider, medication container or the like. While the system professes to ensure adherence to a protocol, the system only provides such help if requested by a user. There is in fact no particular manner in which to ensure actual adherence or ingestion of the medication, or the relationship of adherence to the efficacy or safety of the drug over time. When requiring adherence to a predetermined protocol for a clinical trial, this is particularly relevant.

Additionally, existing systems fail to maintain an audit trail for post administration review by a medical official or other clinical trial administrator, and further cannot therefore confirm confirmation of proper medication administration or population management.

Therefore, it would be desirable to provide an apparatus that overcomes the drawbacks of the prior art.

SUMMARY OF THE INVENTION

In U.S. patent application Ser. No. 12/620,686, filed Nov. 18, 2009, titled Method and Apparatus for Verification of Medication Administration Adherence; currently pending, U.S. patent application Ser. No. 12/646,383, filed Dec. 23, 2009, titled Method and Apparatus for Verification of Clinical Trial Adherence, currently pending; U.S. patent application Ser. No. 12/646,603, filed Dec. 23, 2009, titled Method and Apparatus for Management of Clinical Trials, currently pending; and U.S. patent application Ser. No. 12/728,721, filed Mar. 22, 2010, titled Apparatus and Method for Collection of Protocol Adherence Data, currently pending, the contents of these four applications being incorporated herein by reference, the inventors of the present invention have proposed a system, method and apparatus that allow for complete control and verification of adherence to a prescribed medication protocol or machine or apparatus use in a clinical trial setting, whether in a health care provider's care, or when self administered in a homecare situation by a patient.

These applications present the only medication management system that may determine whether a user is actually following a protocol, provide additional assistance to a user, starting with instructions, video instructions, and the like, and moving up to contact from a medication administrator if it is determined that the user would need such assistance in any medical adherence situation, including clinical trial settings, home care settings, healthcare administration locations, such as nursing homes, clinics, hospitals and the like, and in clinical trial settings.

In accordance with an embodiment of the present invention, a motion capture procedure is proposed to be utilized in accordance with one or more of the inventions noted in the above-referenced applications. Therefore, in accordance with an embodiment of the present invention, a method and apparatus may be provided for analyzing captured patient motion data, transmitting such captured patient motion data to a remote location (or processing such captured information locally, in whole or in part), receiving information from a remote location (or from a processor maintained locally) and providing information to the patient as preferred in accordance with the present invention.

Further in accordance with an embodiment of the present invention, one or more predetermined motion sequences may be determined and correlated to one or more corresponding medication administration instructions. These predetermined motion sequences may be provided as a number of generic motion sequences, as one or more customized motion sequences, or a combination of both. The group of predetermined motion sequences may comprise a motion language that may be applied to one or more different medication administration sequences, healthcare related processes, such as hand washing or the like, medication administration personnel acting as prescribed or the like, thus allowing for an easy to program generic medication administration sequence, but also allow for customization where appropriate and necessary. These programmed motion sequences may then be applied in accordance with the inventions noted in the applications above.

In yet another embodiment of the invention, one or more methods may be provided for confirming that a user is properly performing one or more of these predetermined motion sequences. Thus, as a user positions themselves or an object before an image capture device, a display may indicate to the user whether the position, distance, and/or skew and angle are correct. If not, the user is preferably provided with indications as to how to correct any one or more of these issues.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which.

DETAILED DESCRIPTION OF THE PREFERRED EMBODIMENTS

Figure 1:
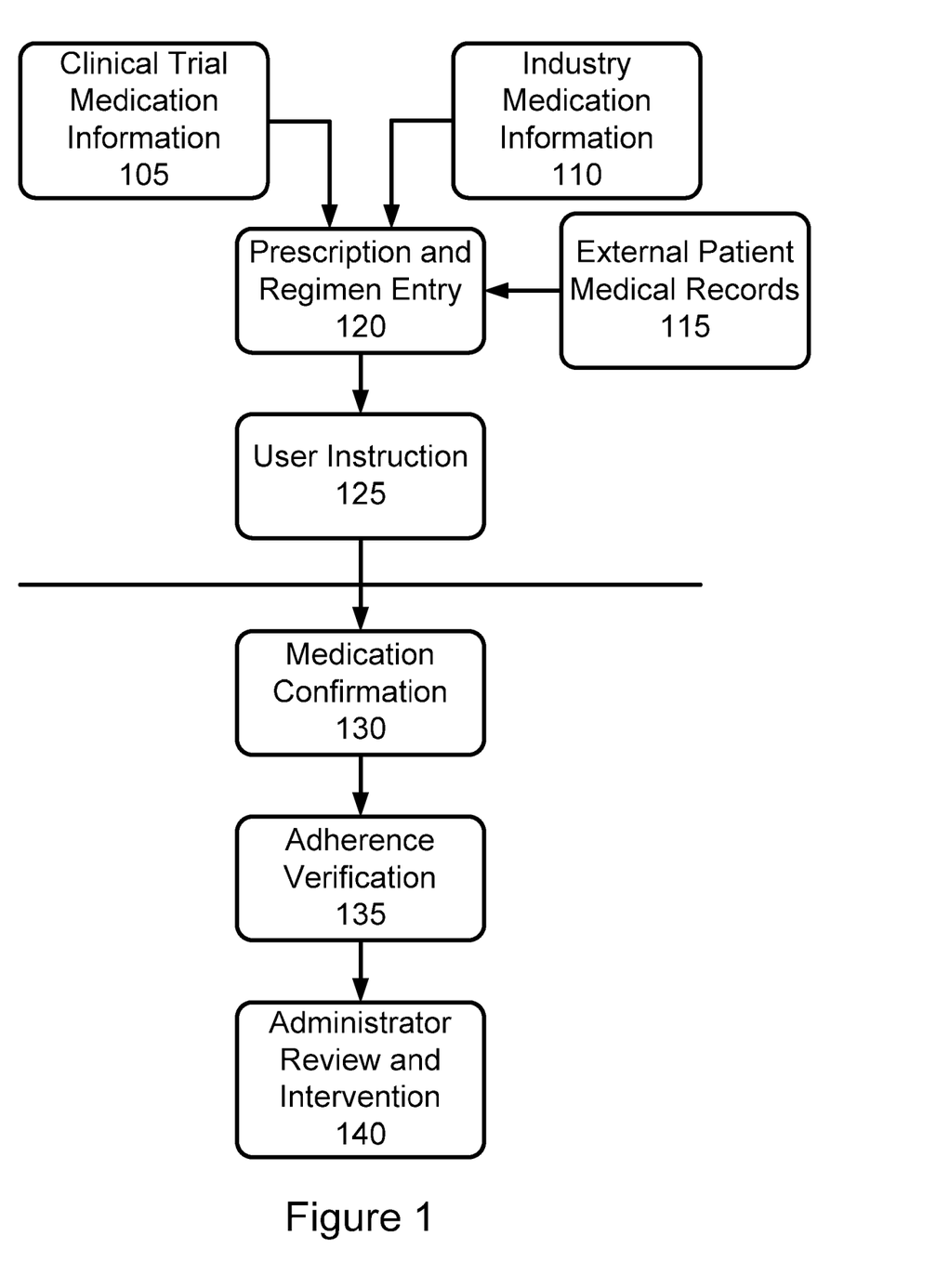
FIG. 1 is a flow chart diagram depicting a method in accordance with an embodiment of the invention.

The invention will now be described making reference to the following drawings in which like reference numbers denote like structure or steps. Referring to FIG. 1, a data flow overview in accordance with the operation of an embodiment of the present invention is shown. In accordance with this embodiment of the invention, information about a particular drug to be the subject of a clinical trial, to be employed in a public health or disease management situation, or the like, or other medication administration program or prescription may be provided in a database 105, and existing industry medication information databases 110 are preferably employed to access prescription, interaction, application, and other available information about any number of proposed prescription and non-prescription medications and their possible interaction with the clinical trial or other medications. Further, patient medical records 115 may be used, and as will be described below, are used in conjunction with the industry medical information and a medical professional's prescribing expertise to confirm that a patient is a good candidate for such a clinical trial, or medication administration program. These databases may be accessed in a manner known to one of ordinary skill in the art.

Once confirmed, a medication administration regimen in accordance with the clinical trial or other prescription requirements may be prescribed and entered into the system of the invention at 120. Once entered into the system, a particular prescription regimen may cause a set of user instructions 125 to be generated and transmitted to an apparatus provided to a patient in accordance with an embodiment of the invention for access to the system of the invention. Such an apparatus may comprise a custom designed video capture, analysis and transmission apparatus, a smart phone or other mobile device including a camera or other video capture apparatus, a netbook, laptop computer, desktop computer, tablet device or the like, or other computing appliance allowing for the display of instructions to a patient, and allowing for the eventual capture, analysis and transmission of video and other analysis information. When installing software on a user's own hardware system, it is preferred that the software detect and otherwise test or determine that the hardware attempting to be utilized by the patient is sufficient to implement the invention and is sufficient to run a software package provided in accordance with the invention. Thus, the software may check that a camera includes sufficient resolution, that a memory of the device is of sufficient size to allow for sufficient captured video storage, and that the transmission system includes sufficient bandwidth to transmit and receive captured video, video instructions and the like.

In a clinical trial setting, patient instructions may be varied for different users to determine the best set of instructions, or may be varied based upon demographics, experience, or other factors that may require different types of instructions to be provided. It is further contemplated in accordance with an embodiment of the invention that multiple clinical trials or patient populations may be managed by a manager in accordance with the invention so that the invention contemplates a medication administration system that allows for a single point of management for all clinical trials or patient management groups associated with a particular manager or the like. Such management techniques in accordance with the embodiment of the invention may further be applied to various public health situations, disease management scenarios and the like.

Such user instructions may include general instructions about the particular medication subject to the current trial or medication administration protocol, methods for ingestion, warnings about side effects, and concerns about drug interactions with common substances or medications, or other medications prescribed to the patient by the system or by another medical service provider. It is contemplated in accordance with an embodiment of the invention that such set of user instructions may be interactive, allowing a user to view additional information about such instructions or prescriptions as desired. These instructions may comprise written, audio or video instructions provided to the user on a display of the user apparatus. It is further contemplated that such instructions may indicate one or more movement sequences to be associated with a corresponding one or more medication administration sequences. A more in-depth description of the information provided at step 125 is depicted in FIG. 2.

Figure 2:
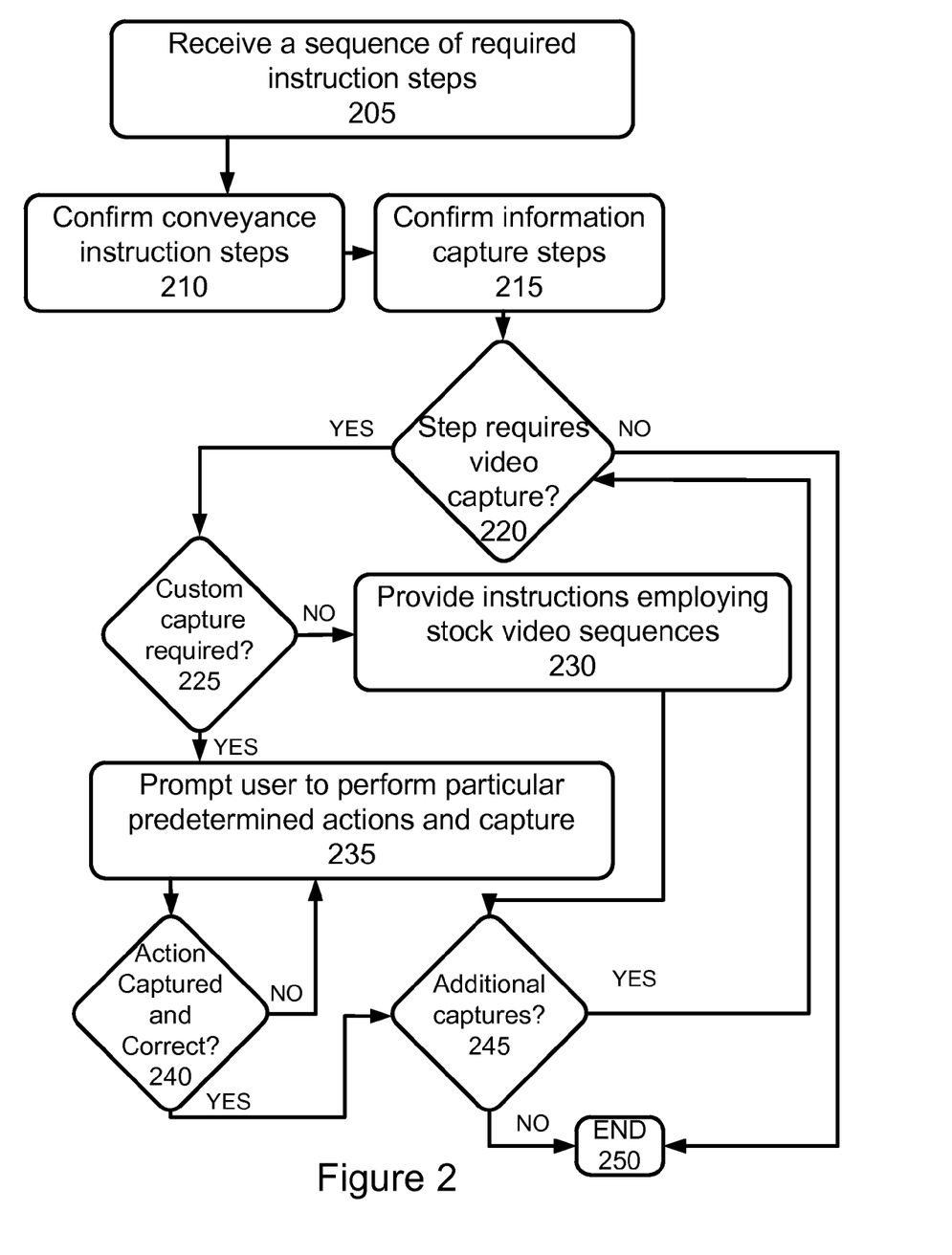
FIG. 2 is a flowchart diagram depicting a video sequence generation method in accordance with an embodiment of the invention.

As is shown in FIG. 2, the generation and provision of user instructions as set forth in step 125 first comprises the step of receiving a sequence of required instruction steps at step 205. This sequence may be determined as described above in step 120. The system then may confirm whether one or more of the instructions steps require the conveyance of information to a patient at step 210. These conveyance steps may comprise a more conventional instruction step, such as the display of written information, comprise a more advanced instruction step, such as the conveyance of audible information, video instructions or the like, or may comprise an inventive instruction step, including the eventual capture of information from the user. Thus, at step 215, it may be determined whether one or more of the instruction steps will require the capture of information from the user. Thereafter, each of the steps requiring capture of video information from a user is confirmed at step 220. If no such video capture is required, processing for step 125 then ends. If it is determined that the capture of video information will be required at step 220 for the current instruction capture step, then processing passes to step 225 where it may be determined whether a custom video capture is required. If it is determined that the video information capture does not require custom video sequences, then processing passes to step 230, and various stock video sequences are determined corresponding to the video capture information step noted at step 220.

If it is determined, however, at step 225 that a custom video capture is required, then processing passes to step 235 where the user may be prompted, by being shown one or more stock video instruction sequences or other appropriate instruction indication, to perform a particular action or sequence of movements. The user may request to be re-shown these sequences as many times as necessary, and may also include audio or other instructions, so that the user is provided with a training sequence, thereby reducing variability of future performance of that action. When preparing to perform these actions, an alert system may be employed to warn the patient of any issues that may interfere with the proper capture of video information.

Figure 4:
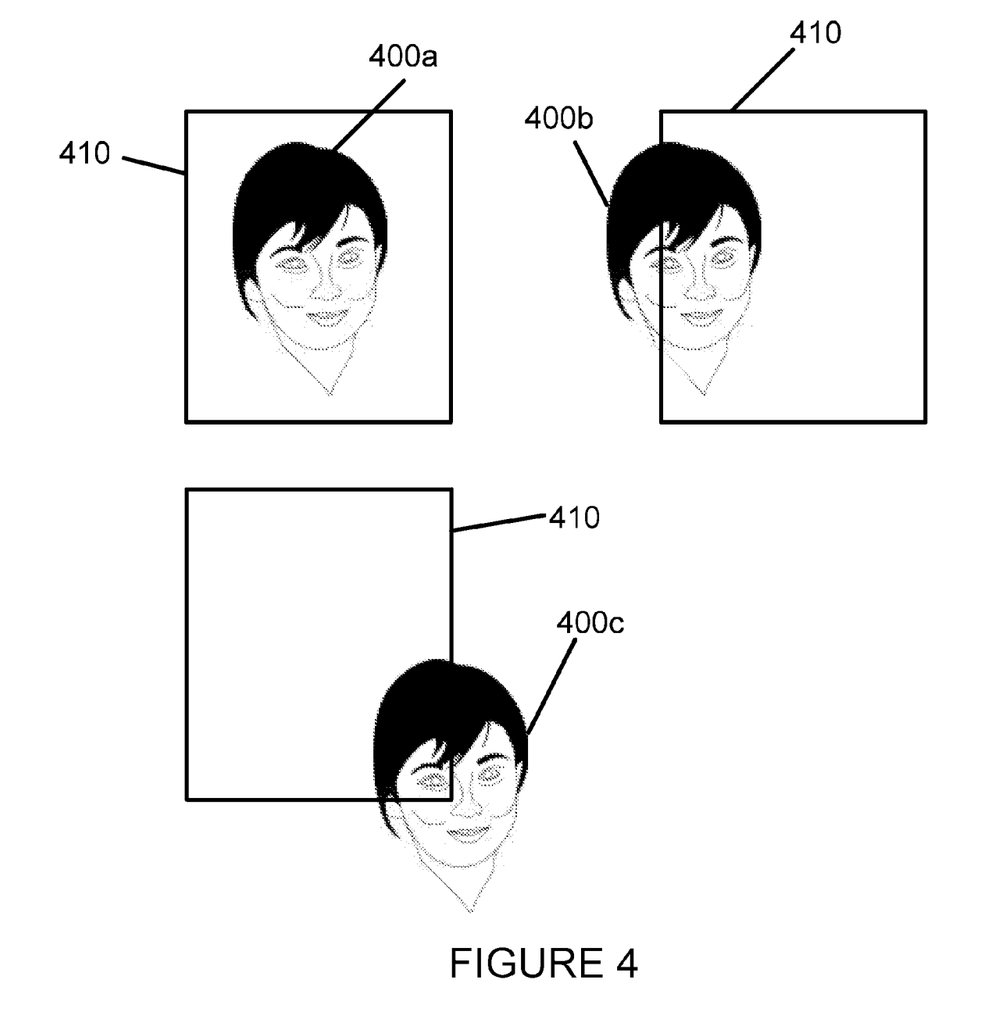
FIG. 4 is a depiction of a positioning process in accordance with an embodiment.

Thus, the user may be notified if they are sitting in a manner in which their actions cannot be properly captured, if they are blocked from the camera, the light conditions are insufficient, if an object they are holding is in an improper location, or the like. As is shown in FIG. 4, a box 410 may be provided on a display viewable by a patient using the system. A representation of the patient's face may be shown in a position relative to an optimal filming position. Thus, while facial representation 400*a* is properly positioned, facial representation 400*b* is positioned to the left of the box, while facial representation 400*c* is positioned down and to the right of the box. In practice, the box may be made a red or other warning color until proper alignment is achieved (including if a user is not positioned fully within a screen, the user is too close or far from the camera, or for any other reason), at which time the box may change to green or other appropriate color. Further, audio clues may also be given to the patient, such as increasing frequency beeping as the optimal position is approached. Thus, in accordance with an embodiment of the present invention. The user is provided with immediate feedback on their position and the ability of their actions to be properly recorded and analyzed. As the user interacts with the system of this embodiment of the invention, such a scheme may be employed to provide continuous feedback to the user, and thus indicating whether the system is able to properly capture and/pr analyze the actions of the user. If time is passed and the user is unable to properly position themselves, or to properly perform desired actions, additional guidance may be provided to the user in order to remedy such a situation, including but not limited to directional indications, voice commands, video images of proper technique, etc.

Figure 5:
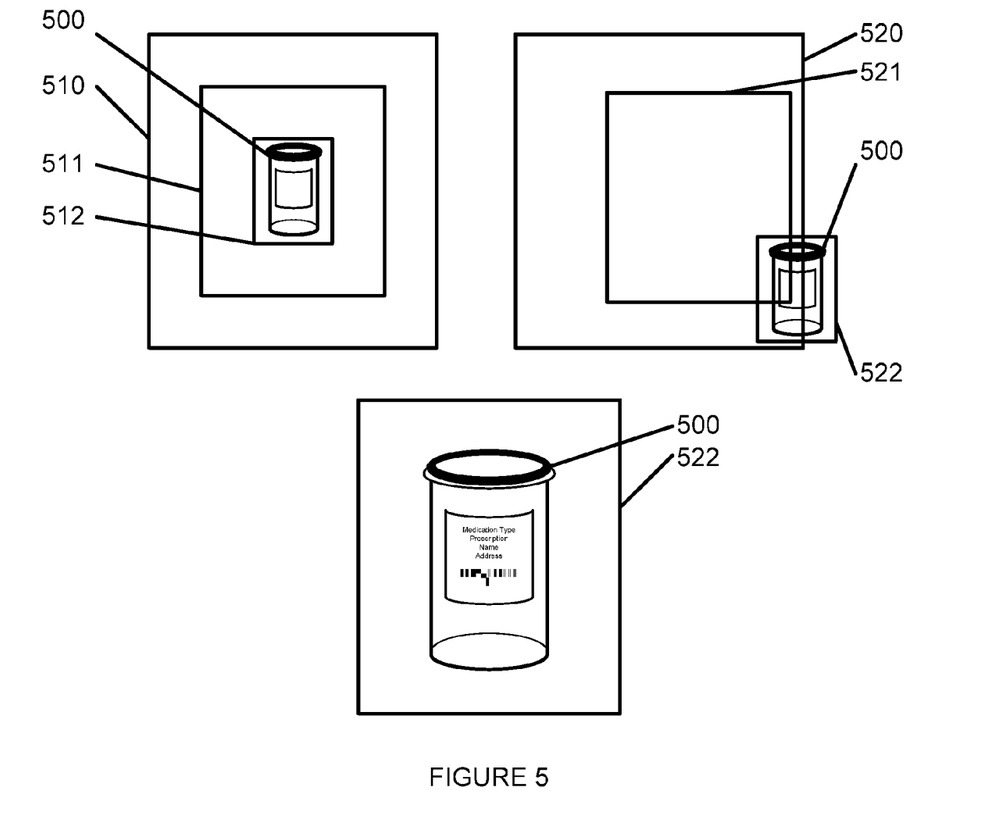
FIG. 5 is a depiction of another positioning process in accordance with an embodiment of the invention.

In addition to properly positioning the patient, proper positioning of one or more objects may be determined, such as positioning a pill bottle or pill tablet for imaging and processing in accordance with an embodiment of the invention. As is shown in FIG. 5, a pill bottle 500 may be indicated as properly positioned by a box 522, the box being green, for example, as in the description of FIG. 4. Such an object, however, is more likely to be improperly positioned not only left to right and up to down, but also in distance to the imaging apparatus, in accordance with one or more limitations of the imaging device, such as the resolution thereof, low light positions, and the like, and any affect such resolution might have on the ability of the imaging device to identify shape, color text or other coding, or the like associated with the object being imaged. Thus, if positioned too far away from the imaging apparatus, a sequence of boxed 510, 511, 512 and a small representation of pill bottle 500 may be provided to alert the user to move the pill bottle closer. If the pill bottle is not only too far away, but off center, boxes 520, 521, 522 may be provided to guide the user to move the bottle into proper position. The apparatus, in accordance with an embodiment of the invention, may thus ask the user to move the bottle closer to or further away from the imaging apparatus, may change an ambient light sensitivity of the apparatus, or may otherwise change details of the image capture. As noted above, both color and audio prompting may be provided.

Figure 6:
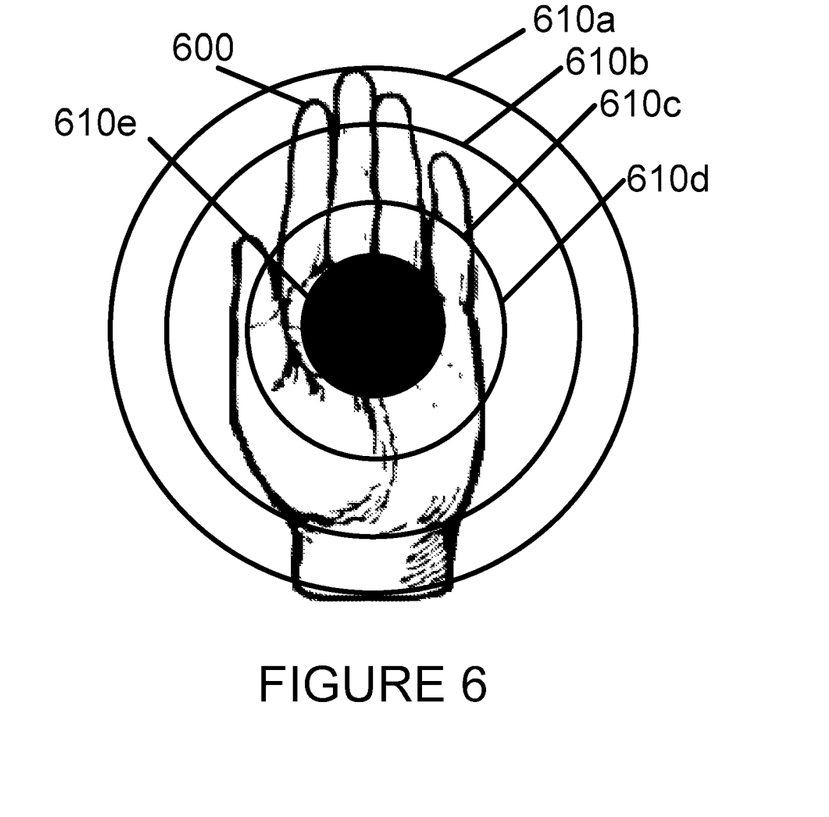
FIG. 6 is a depiction of yet another positioning process in accordance with an embodiment of the invention.

To the extent that any hand positioning is important, such as a user being requested to display an open palm after taking medication, a similar system may be employed. As is shown in FIG. 6, a set of concentric circles 610 *a-e* may be provided to aid in the positioning of hand 600. A center circle 610*e* may be provided with a solid center upon proper placement of the hand. These circles may move as the boxes in FIG. 5, and may further use color and/or audio prompts to instruct the user. Further, as images of hand positions, or images of hands containing pills therein, are to be captured and analyzed, the system may also preferably indicate not only proper positioning, but actual acquisition of a recognizable gesture. In accordance with an additional embodiment of the invention, such recognizable gesture may further comprise a sequence of gestures employed to ensure that the patient properly ingests or otherwise administers their medication. In accordance with an ingestion process, the patient may first be trained to show a particular pill in their open hand to the camera for imaging and recognition. The user may then be asked to place the pill between their fingers, place the pill in their mouth, show an empty palm to the camera, and take a drink from a glass of water of the like to finally confirm ingestion. Thus, through a predetermined sequence of actions that are captured, imaged and analyzed, evidence of proper administration can be recorded and analyzed.

Figure 7:
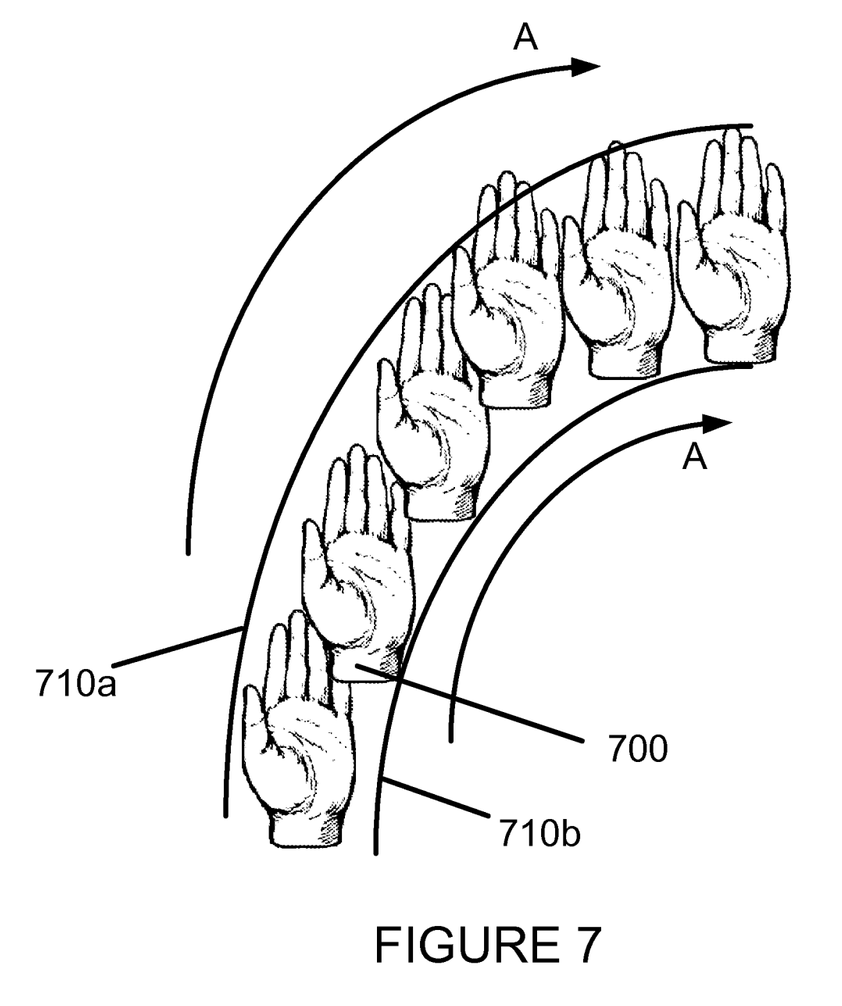
FIG. 7 is a depiction of a motion tracking process in accordance with an embodiment of the invention.

Furthermore, as is shown in FIG. 7, when tracking the movement of a hand 700, if is preferable to depict to a patient whether they are moving their hand correctly. Thus, as is show in FIG. 7, a hand 700 is indicated to move in the direction noted by arrows A. A set of guidance tracks 710*a*, 710*b* may be displayed to a patient and successive hand positions may be superimposed thereon. As the hand moves along the proscribed path, concentric circles such as those depicted in FIG. 6 may be employed to confirm proper location. Thus, in accordance with an embodiment of the invention, a virtual path may be shown to the user to ensure that the proper method of medication administration is followed. As noted above, color and/or audio sequences may also be employed.

Therefore, in accordance with one or more of the positioning assistance schemes noted in FIGS. 4-7, a patient may be guided to properly present themselves or an object to an image capture device for capture and interpretation. Any of the display and notification techniques noted in any of these Figures may be used in any of the other Figures, in accordance with various embodiments of the invention. Further, these positioning techniques may be employed not only during initial sequence capture, but during any subsequent system process employing video image capture of people, objects, or any other entity to be imaged.

Referring back to FIG. 2, at step 240 these motions of the user may be captured and confirmed as being correct, either by comparison with the stock sequences, or by confirmation by an administering individual. If not correct, processing may return to step 235 to provide the example sequences again to the user. Therefore, in accordance with the invention, and as noted above, while custom video sequences may be used, repeated instruction may be once again provided to the patient, thereby aiding in limiting future variability in the actions taken by the patient during administration. Such instruction may take the form of analysis of a recorded user action, and comments on what the user may be doing wrong, and how this action may be improved. Once the user has received sufficient instruction, and it is therefore determined that the user has performed the action in a manner that is sufficiently similar to the instruction set, and substantially consistent over a number of performances of the action, the user sequences may be captured to act as future standards against which the user's actions during medication administration can be compared. If the sequences are captured and determined to be correct at step 240, processing then passes to step 245 where it is determined whether there are additional video sequences to be captured. If so, processing returns to step 220 for further processing. If not, processing ends at step 250.

Referring back to the lower portion of FIG. 1, the horizontal line indicates a time for patient ingestion or other administration of medication. While not explicitly shown, first, preferably the identity of a user is confirmed through the use of a facial recognition sequence, other biometric identification sequence, or other password identification system. Upon recognition of the individual, the system may display one or more data regarding the individual, such as, by way of example only, name, patient status, medication to be administered, calendar indicating to the patient when medication has been administered and if any administration times have been missed, and, selectively, a score indicative of a level of compliance of the individual with the medication protocol. Once identified and notified of a type of medication to be administered, the patient may display a medication container and/or an actual pill or other medication form to confirm that the medication is correct and is the currently prescribed medication to be taken through the use of text recognition, pill recognition, barcode or other code reading of one or more unique identifiers from the medicine bottle or the like, or other appropriate medication recognition scheme. The user may alternatively be shown a virtual pill box with visual or textual indications of one or more pills to be taken at a particular time. Imaging of one or more of such pills may then match a pill provided by the patient to one or more of the pills in the virtual pill box. Thus, the patient is not only allowed to have a particular pill imaged, but also may be given a visual representation of pills to be taken, pills that have already been taken, and a visual picture of one or more additional pills to look for if the patient is confused or is not immediately able to locate all of the required medication. Such a display may further act as an additional incentive program for the patient to properly take their medication, and may in turn give a patient other incentives, such as a running score, payment information or other point systems if the patient is to be rewarded for properly taking medication. The display of such information may assist in convincing the patient to continue to properly take medication. This sequence of steps therefore acts as an audit trail each time a medication is taken, that can be reviewed later, to ensure that a patient is properly following a regimen. Any of the positioning schemes depicted in FIGS. 4-7 may be employed.

In accordance with the invention, confirmation of patient adherence to the prescribed administration schedule for the medication as prescribed by the clinical trial or other prescription regimen may be determined. While such confirmation may take a number of forms, in accordance with the invention, a preferred method for such confirmation may include capturing a video sequence of the patient actually administering the medication. In a further preferred method, such a sequence for such confirmation may include employing a facial recognition sequence or other biometric confirmation that a particular patient is in fact receiving treatment, but may also provide for the ability to obscure the face or other identifying feature of a user, or otherwise encrypt such information to allow for the storage and use of such images while protecting the identity of the patient, a technique that may be beneficial when a medication administration manager is providing a general report about a clinical trial, and not trying to remedy a situation with a particular patient, or in particular in a public health or disease management scenario. Activity recognition, gesture recognition or other feature for determining whether a particular subject movement meets a predefined movement sequence may be employed to be sure that the patient is properly taking prescribed medication.

Figure 3:
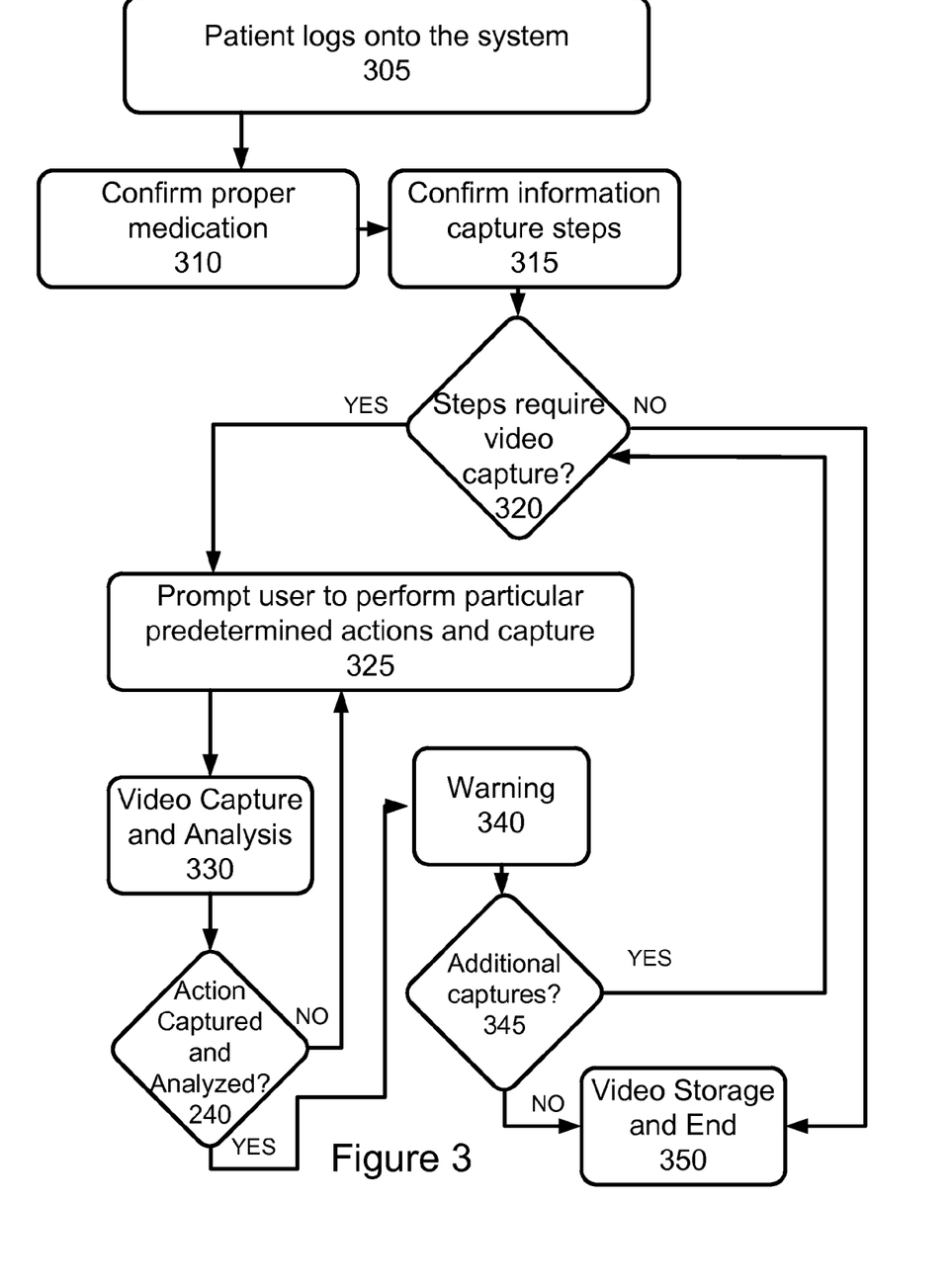
FIG. 3 is a flowchart diagram depicting a video sequence capture method in accordance with an embodiment of the invention.

Referring next to FIG. 3, a method in accordance with an additional embodiment of the present invention for performing video capture and recognition of adherence to a prescribed protocol is described, as set forth in steps 130 and 135 of FIG. 1. In FIG. 3, a patient may first log into the system of the invention at step 305, employing the facial recognition, biometric recognition, password entry, or other patient identification method, and at step 310 proper medication is confirmed as noted above, through the user of bar code reading, text recognition, visual recognition employing video or still image recognition, or other medication recognition technique. Of course, any of the positioning techniques previously described in reference to FIGS. 4-7 may be employed. Next, at step 315 it may be confirmed that the process involved will include one or more information capture steps, and at step 320 it may be determined whether these information steps will include video capture. If not, video processing ends after storage of any non-video information. If it is confirmed at step 320 that one or more steps will include video capture, processing then passes to step 325 where the user may be prompted to perform one or more predetermined actions, these actions being captured. Positioning may be performed in accordance with any of the techniques as described previously in reference to FIGS. 4-7. Further, voice recognition may be utilized to allow the user to enter commands, and an audio output may be provided for aiding the user in properly adhering to instructions from the system. Proper capture of patient actions are very important as the patient only administers the medication once per capture period.

Video capture analysis may then begin at step 330, such analysis comprising comparison of the newly captured video with either stock video sequences or custom recorded video sequences, as provided as noted above with respect to FIG. 2. At step 335 it may be determined whether the action has been properly captured, and whether the captured action has been properly analyzed by the system. Various incentives may be provided to the patient to encourage them to take their medication properly. Thus, in addition to providing various reminders to a patient as is known in the art, points, monetary or other incentive may be provided to the user for actually having medication administration confirmed. Further proper administration with less errors, etc. may be rewarded more highly, thus giving incentive for the patient to concentrate on administration issues and to attempt to have such administration be as accurate and consistent as possible. Such incentives and medication tracking may be used to determine future courses of treatment or payment. For example, if a patient consistently fails to take medication as required, perhaps a different course of treatment requiring fewer medication administrations may be better for this patient. Alternatively, if a medication requires a consistent administration and is very expensive, failure to comply with administration instructions may be cause for an insurance company, prescribing doctor or the like to not renew such a prescription for the patient, thus saving money in a situation where the money was being wasted because of lack of compliance.

If it is determined that administration of the medication did not take place properly, processing may return to step 325 and the user may be once again prompted to perform the action. Of course, if this process involves actual ingestion of medication, it may not be proper to request re-performance of the action, unless it can be determined that the user did not ingest the medication previously. If the action has been properly captured, and is able to be analyzed, processing passes to step 345 where it may be determined whether additional captures are required. If so, processing returns to step 320. If no further captures are required, processing ends at step 350 where the various captured video sequences are stored. These stored sequences may also be made available for human review and involvement, when it is determined that this would be beneficial.

Therefore, in accordance with various embodiments of the invention, because a video image of the patient actually administering or ingesting the medication (or other method of medication administration, including but not limited to injections, dialysis, and any other medication administration procedure) may be captured and analyzed, actual confirmation may be achieved, rather than simply relying on the patient to state that a particular medication was administered. Such a video image may be captured or stored in any appropriate format given a selected type of activity or gesture recognition that is employed in accordance with a particular embodiment of the invention. Such may include full video, biometric data points, recording of movement of an article, such as a bracelet or the like, affixed to the patient or administrator, use of mapping to provide a stick figure or other body movement tracking technique, or gesture or activity recognition to determine movement or the like. The user may be encouraged to use a particular sequence of movement to be confirmed that they are properly administering the medication according to the protocol, thus reducing the possibility of the potential appropriate movements considered to be "correct." Or, as noted above, capture of customized video sequences may be performed so that the user is more likely to repeat these same actions. Indeed, various instructional videos or other appropriate training may be provided to a user to insure they properly administer the medication.

Through the use of a combination of stock and custom video sequences for comparison and analysis to a newly captured patient movement sequence, a type of administration language may be generated, allowing for extension to other patients, and also allowing for interpretation of reason for differences from a predefined sequence by a patient. Thus, if a patient performs an action differently over time, this difference may provide insight to a reaction to a medication, changes in the patient's medical condition, or the like. It is further anticipated that analysis of large numbers of patients will allow for a more flexible system that may recognize more of a patient's movements as compared to a stock video sequence, and thus may improve the ability of the system to function without needing to take up front custom video captures for each and every administration step.

Therefore, in accordance with an embodiment of the invention, a user may perform a predetermined sequence of actions designed to ensure performance of medication administration. Thus, by way of example only, for an ingested medication as noted above, the user may be asked to first show a medication in their palm, between their fingers, or in other display methods, may then be prompted to ingest the medication as indicated by movement of the user's hand to their mouth. Next the user may be prompted to display an empty hand to the capture device, asked to show their mouth to confirm it is empty, and finally asked to drink a bit of water and to have the water level monitored to aid in confirming that the patient in fact has taken their medication. Of course, in accordance with this embodiment of the invention, other action sequences may be employed, and may be mixed with other actions to be performed by a patient or caregiver. Thus, but defining a medication adherence protocol as a single or sequence of gestures that may be recognized by a processing system, the accuracy of confirming that a patient has actually taken a particular medication is improved. Through an interactive learning process, the processing system may also learn patient behaviors to be more accurately determine medication adherence, and to remove some of the potential false positives or false negatives. If a caregiver is involved, it is contemplated that the caregiver be provided with a number of gestures indicative of particular actions to be taken, and use of these gestures prompting the system to confirm that these actions are in fact being taken. Thus, a full audit trail of not only the patient, but also the caregiver may be determine, such as whether they approached the patient at the correct times, or that they washed their hands when approaching.

Further uses of the video capture sequences may also be employed, including video capture of responses to questionnaires about current patient states of discomfort, informed consent, example of questions to be asked, video transmission of such questions and the like. The patient may be able to send a video message, pointing to a particular pain or the like, and may include an audio portion as well. Time stamp markers may also be captured to confirm that the user is taking their medication at appropriate times and a number of times a user has taken a particular medication, to confirm whether there are substantial delays between instruction and administration, or for any other time sequence determination. Furthermore, other behavioral markers, such as, by way of example only, shaking hands indicating a particular ailment, or other movements by a patient that may give a hint as to the physical or mental status thereof. Additionally, if the user is taking medication that is improper, or they have already taken, a warning may be provided to warn the user to stop medication administration immediately.

It is further contemplated that the method and apparatus of the invention allow for integration with one or more audio or video conferencing systems, thus receiving and/or providing information there through. Thus, a user may employ a standard video conferencing tool or system, and have this information be coupled to a mobile or other device being used in accordance with an embodiment of the present invention.

Therefore, in accordance with the invention, a method and apparatus are provided that allow for the automated confirmation of adherence to administration protocol for medication, and provide for a most sophisticated method for confirming and studying methods of administration of such prescription medication.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that this description is intended to cover all of the generic and specific features of the invention herein described and all statements of the scope of the invention which, as a matter of language, might be said to fall there between.

What is claimed:

1. A medication administration confirmation apparatus, comprising:
    a memory for storing on a local device a predetermined video sequence corresponding to a particular predetermined prescription regimen, the predetermined video sequence further comprising a plurality of predetermined video steps;
    a display associated with the local device for displaying one or more instruction prompts associated with each of the plurality of predetermined video steps of the stored predetermined video sequence, and for displaying one or more graphical guidance indicators directing movement in accordance with each of the plurality of predetermined video steps of the stored predetermined video sequence;
    a video capture device associated with the local device for sequentially capturing one or more video sequences of a user administering medication following the one or more instruction prompts and one or more guidance indicators to a video capture memory associated with the local device; and
    a processor associated with the local device, wherein the processor is operable to:
        a) output to the display at least one instruction prompt instructing the user to perform one or more actions and at least one graphical guidance indicator guiding a user's movement relative to the display and/or the video capture device, wherein the at least one instruction prompt and the at least one graphical guidance indicator direct the user to perform motions depicted in a corresponding predetermined video step of the predetermined video sequence,
        b) receive from the video capture device the sequentially captured one or more video sequences following the output of the at least one instruction prompt and the at least one guidance indicator to the display,
        c) in response to receiving the sequentially captured one or more video sequences, compare, in accordance with one or more of facial recognition, activity recognition or gesture recognition, at least one of the sequentially captured video sequences to a corresponding predetermined video sequence of the predetermined video sequence,
        d) determine, from the comparison, whether the user incorrectly followed a step in the predetermined prescription regimen,
        e) in response to determining that the user incorrectly followed the step in the predetermined prescription regimen, output feedback to the display in real time and execute b)-d) again, the feedback comprising a prompt to perform the sequence of actions for following the predetermined prescription regimen again, and
        f) in response to determining that the user correctly followed the step in the predetermined prescription regimen, output to the display at least one other instruction prompt and at least one other guidance indicator, wherein each of the at least one other instruction prompt and the at least one other guidance indicator direct the user to perform motions depicted on the display and associated with a next predetermined video step of the predetermined video sequence.

2. The medication confirmation apparatus of claim 1, wherein the stored predetermined video sequence is a stock video sequence.

3. The medication confirmation apparatus of claim 1, wherein the stored predetermined video sequence is a prerecorded video sequence of the user administering medication.

4. The medication confirmation apparatus of claim 1, wherein the at least one instruction prompt instructs a user to perform a particular sequence of actions to be stored as the one or more video sequences.

5. The medication confirmation apparatus of claim 4, wherein the particular sequence of actions is designed to assist in determining proper medication administration.

6. The medication confirmation apparatus of claim 1, further comprising a data transmission system operable to transmit one or more of the at least one or more stored video sequences to a remote location for analysis.

7. The medication confirmation apparatus of claim 6, further comprising a data reception system operable to receive information from the remote location.

8. A medication administration confirmation method employing a computing device, comprising:
    a) outputting, from a processor of the computing device, to a display communicatively coupled to the computing device, one or more instruction prompts that direct a user to perform one or more actions in a step of a plurality of predetermined steps indicative of proper administration of medication according to a particular predetermined prescription regimen, wherein the one or more actions in the step comprise motions depicted in a corresponding predetermined video sequence;
    b) capturing by a video capture device associated with the computing device a video sequence of a user performing the step of the plurality of predetermined steps indicative of the user properly administering medication following the display of the one or more instruction prompts, in accordance with a the particular predetermined prescription regimen;
    c) storing the captured video sequence to a computer readable non-transitory storage medium associated with the computing device;
    d) comparing automatically by the computing device, in accordance with one or more of facial recognition, activity recognition and gesture recognition, the captured video sequence upon capture thereof to the corresponding predetermined video sequence, to determine if the step of the plurality of predetermined steps indicative of administration of the medication has been performed incorrectly;
    e) responsive to determining that the step of the plurality of predetermined steps has been performed by the user incorrectly, outputting, from the processor to the display, feedback to the user in real time, the feedback comprising one or more instruction prompts to prompt the user to perform the step of the plurality of predetermined steps again, and performing by the processor b)-d) again;
    f) responsive to determining that the step of the plurality of predetermined steps has been performed by the user correctly, performing by the processor a)-f) for a next step of the plurality of predetermined steps or confirming by the processor that the user has properly performed the predetermined steps indicative of proper medication administration.

9. The method of claim 8, further comprising storing at least one stock video sequence to be employed when comparing the captured video sequence to the corresponding predetermined video sequence.

10. The method of claim 8, further comprising storing at least one prerecorded video sequence of the user administering medication to be employed when comparing the captured video sequence to the corresponding predetermined video sequence.

11. The method of claim 8, further comprising outputting from the processor to the display the one or more instruction prompts to the user to perform a particular sequence of actions to be stored as a prerecorded video sequence of the user administering medication to be employed when comparing the captured video sequence to the corresponding predetermined video sequence.

12. The method of claim 11, wherein the particular sequence of actions is designed to assist in determining proper medication administration.

13. The method of claim 12, wherein the particular sequence of actions further comprises:
displaying a medication between the fingers of a user;
placing the medication in the mouth of the user;
displaying an empty mouth of the user after medication ingestion; and
drinking water after display of the empty mouth.

14. The method of claim 8, further comprising transmitting the captured video sequence to a remote location for analysis.

15. The method of claim 14, further comprising receiving information from the remote location.

16. A medication administration confirmation method, comprising:
a) determining, by a processor associated with a local device, a sequence of a plurality of steps to be performed by a user indicative of ingestion of a medication;
b) outputting from the processor to a display on the local device at least one instruction prompt and at least one graphical guidance indicator to aid in proper performance of each step of the determined sequence of steps, wherein the at least one instruction prompt and the at least one graphical guidance indicator direct the user to perform motions depicted in a corresponding predetermined video steps of the predetermined video sequence;
c) capturing, by a video capture device associated with the local device, performance of a step of the determined sequence of steps;
d) storing the captured performed step of the determined sequence of steps to a computer readable, non-transitory storage medium associated with the local device;
e) determining automatically by the processor, in accordance with one or more of facial recognition, activity recognition and gesture recognition, whether the captured performed step of the determined sequence of steps has been performed by the user incorrectly using facial recognition, activity recognition and/or gesture recognition;
f) responsive to determining that the step of the determined sequence of steps has been performed by the user incorrectly, providing from the processor feedback to the display of the local device, the feedback comprising a further one or more instruction prompts and graphical guidance indicators to further aid in proper performance of the step of the determined sequence of steps, and performing by the processor in real time b)-e) again;
g) responsive to determining that the step of the determined sequence of steps has been performed correctly, performing by the processor b)-g) for a next available step of the predetermined steps or confirming by the processor that the user has properly administered the medication when each step in the sequence of the plurality of steps has been performed correctly.

17. The method of claim 16, wherein the determined sequence of a plurality of steps to be performed by the user indicative of ingestion of the medication further comprises:
displaying a medication between the fingers of the user;
placing the medication in the mouth of the user;
displaying an empty mouth of the user after medication ingestion; and
drinking water after display of the empty mouth.

18. The method of claim 17, wherein for each step of the plurality of steps, the processor outputs to the display a corresponding instruction prompt indicating where the user is to move their hand.

19. The method of claim 17, further comprising transmitting at least one of the captured plurality of the determined sequence of steps to a remote location for further analysis.

20. The method of claim 17, further comprising notifying an administrator and the patient if it is determined that a user has not properly administered the medication.

* * * * *